(12) United States Patent
Chen et al.

(10) Patent No.: US 12,359,246 B2
(45) Date of Patent: Jul. 15, 2025

(54) METHOD, KIT AND SYSTEM FOR END LABELING OF NUCLEIC ACIDS

(71) Applicant: Cheng-Yao Chen, Hsinchu (TW)

(72) Inventors: Cheng-Yao Chen, Hsinchu (TW); Yi-Wen Cheng, Hsinchu (TW)

(73) Assignee: Cheng-Yao Chen, Hsinchu (TW)

( * ) Notice: Subject to any disclaimer, the term of this patent is extended or adjusted under 35 U.S.C. 154(b) by 0 days.

(21) Appl. No.: 18/900,948

(22) Filed: Sep. 30, 2024

(65) Prior Publication Data

US 2025/0019744 A1   Jan. 16, 2025

Related U.S. Application Data

(63) Continuation of application No. PCT/US2023/074293, filed on Sep. 15, 2023.

(60) Provisional application No. 63/406,941, filed on Sep. 15, 2022.

(51) Int. Cl.
   *C12Q 1/68* (2018.01)
   *C12Q 1/44* (2006.01)
   *C12Q 1/6806* (2018.01)

(52) U.S. Cl.
   CPC ............ *C12Q 1/6806* (2013.01); *C12Q 1/44* (2013.01)

(58) Field of Classification Search
   CPC .................................................. C12Q 1/6806
   See application file for complete search history.

(56) References Cited

U.S. PATENT DOCUMENTS

| | | | |
|---|---|---|---|
| 2002/0155573 A1* | 10/2002 | Lanes | C12N 9/2497 435/6.13 |
| 2004/0005614 A1 | 1/2004 | Kurn | |
| 2019/0211386 A1* | 7/2019 | Ward | C12Q 1/6853 |

OTHER PUBLICATIONS

Xu et al., "Biochemical and Mutational Studies of the 5'-3' Exonuclease of DNA Polymerase I of *Escherichia coli*", Journal of Molecular Biology, 1997, pp. 284-302, DOI: https://doi.org/10.1006/jmbi.1997.0967.

Wang et al., "*Staphylococcus aureus* protein SAUGI acts as a uracil-DNA glycosylase inhibitor", Nucleic Acids Research, Oct. 22, 2013, pp. 1354-1364, vol. 42, No. 2, DOI: https://doi.org/10.1093/nar/gkt964.

"International Search Report" mailed on Feb. 21, 2024 for International application No. PCT/US2023/074293, International filing date: Sep. 15, 2023.

* cited by examiner

*Primary Examiner* — Kenneth R Horlick
(74) *Attorney, Agent, or Firm* — Winston Hsu

(57) ABSTRACT

Provided is a method for labeling a nucleic acid, including providing a target nucleic acid to be labeled; providing a 5'-end glycosylase to react with the target nucleic acid to create an intermediate nucleic acid having an abasic site at a 5'-end; and providing an aldehyde-reactive compound carrying a detectable label for coupling with the intermediate nucleic acid to form a labeled nucleic acid with the detectable label attached at 5'-end. Also provided are a kit and a system for labeling nucleic acids.

17 Claims, 11 Drawing Sheets

Specification includes a Sequence Listing.

SEQUENCE LISTING

```
Sequence total quantity: 3
SEQ ID NO: 1            moltype = DNA  length = 45
FEATURE                 Location/Qualifiers
modified_base           1
                        mod_base = OTHER
                        note = uracil
source                  1..45
                        mol_type = other DNA
                        organism = synthetic construct
misc_feature            1
                        note = RNA
misc_feature            2..45
                        note = DNA
SEQUENCE: 1
tctcggcctg gcacaggtcc gtctcagtgc tgcggcgacc accga              45

SEQ ID NO: 2            moltype = DNA  length = 15
FEATURE                 Location/Qualifiers
source                  1..15
                        mol_type = other DNA
                        organism = synthetic construct
SEQUENCE: 2
tgtgccaggc cgaga                                               15

SEQ ID NO: 3            moltype = DNA  length = 47
```

```
FEATURE            Location/Qualifiers
modified_base      1
                   mod_base = OTHER
                   note = uracil
source             1..47
                   mol_type = other DNA
                   organism = synthetic construct
misc_feature       1
                   note = RNA
misc_feature       2..47
                   note = DNA
SEQUENCE: 3
tctcggcctg gcacaggtcc gtctcagtgc tgcggcgacc accgagg            47
```

METHOD, KIT AND SYSTEM FOR END LABELING OF NUCLEIC ACIDS

CROSS REFERENCE TO RELATED APPLICATIONS

This application is a continuation application of PCT Application No. PCT/US2023/074293, filed on Sep. 15, 2023, which claims the benefit of U.S. Provisional Application No. 63/406,941, filed on Sep. 15, 2022. The contents of these applications are incorporated herein by reference.

SEQUENCE LISTING

This application contains a Sequence Listing XML, which has been submitted electronically and is hereby incorporated by reference in its entirety. The Sequence Listing XML, created on Sep. 14, 2023, is named "YDBL-0001PCTUS-Sequence Listing-20230914.xml" and is 6.13 kb in size.

BACKGROUND OF THE INVENTION

1. Field of the Invention

The present disclosure relates to methods for end labeling of nucleic acids. More particularly, this disclosure relates to methods for creating an abasic site and labeling a chemical or functional moiety at the occurring abasic site at the end of nucleic acids.

2. Description of the Prior Art

Nucleic acids labeling is routinely implemented in biomedical and biological applications, including identification and purification of unknown or target gene fragments, localization of target gene sequences, pinpointing nucleic acids-protein interaction, and visualization of cell and tissue dynamics. Generally, methods for labeling of nucleic acids can be categorized into chemical or enzymatic approaches. The chemical labeling methods involve the modification of the 5'-phosphate group, 3'-hydroxyl group, nucleobase, or sugar moiety of the targeted nucleic acids using chemical-reactive compounds, such as N-(3-dimethylaminopropyl)-N'-ethylcarbodiimide (EDC), imidazole, hydrazine, sodium periodate, and sodium cyanoborohydride, to modify the structure of nucleic acids and subsequently attach a chemical or functional moiety to the desired nucleic acids. On the contrary, the enzymatic nucleic acid labeling methods utilize enzymes, such as alkaline phosphatases, nucleic acid kinases, or DNA/RNA polymerases, to substitute for, add, or incorporate a chemical or functional moiety such as a radioisotope, a biotin group, or a fluorescent-labeled nucleotide to the targeted nucleic acids, thereby attaching a desired label to the nucleic acids.

Although a plethora of nucleic acid labeling techniques are available, these methods normally have lengthy procedures and utilize many types of enzymes, reactive chemicals, or radioactive isotopes, which normally require specialized enzymes, chemicals, or personal training on handling of toxic or radioactive materials and wastes. Furthermore, the labeling efficiency of existing nucleic acid labeling methods varies depending on the length and type of nucleic acids, the position of targeted site to be labeled (e.g., the internal or terminal nucleotide(s) of a nucleic acid sequence), as well as the chemical or functional moieties to be labeled. Therefore, there is still unmet needs for simple, efficient, and eco-friendly nucleic acid labeling methods.

SUMMARY OF THE INVENTION

The present disclosure provides a method for 5'-end labeling of a nucleic acid, the method comprising: providing a target nucleic acid to be labeled; providing a 5'-end glycosylase to react with the target nucleic acid to create an intermediate nucleic acid having an abasic site at the 5'-end of the target nucleic acid; and providing an aldehyde-reactive compound carrying a detectable label for coupling with the intermediate nucleic acid at the abasic site to form a labeled nucleic acid with the detectable label attached at the 5'-end.

In at least an embodiment of the present disclosure, the nucleic acid is single-stranded or comprises at least a duplex region formed by two complimentary strands of nucleic acids. In an embodiment, the nucleic acid is a DNA fragment or an RNA fragment. In another embodiment, the nucleic acid is synthesized de novo or derived from a biological organism. In some embodiments, the nucleic acid is immobilized on a solid-state surface or a polymer surface.

In at least an embodiment of the present disclosure, the aldehyde-reactive compound is a compound having at least one primary amine, a hydrazide, an acylhydrazide, a compound having an aminooxy ($ONH_2$) group, a compound having a naphthalene-containing aminooxy group and/or a compound having a guanidine-containing aminooxy group. In some embodiments, the aldehyde-reactive compound is a hydroxylamine biotin, an aminooxy-poly(ethylene glycol)-azide, an propargyl, an aminooxy-poly(ethylene glycol)-dibenzocyclooctyne (DBCO), an aminooxy-poly(ethylene glycol)-bicyclononyne (BCN), a fluorescent dye-hydroxylamine such as Alexa Fluor™ 488 hydroxylamine, an aldehyde-reactive probe (ARP), an aminooxy-fluorescent dye such as an aminooxy-5 (6)-FAM, an aminooxy-hexachloro-fluorescein (HEX), an aminooxy-5 (6)-ROX and an aminooxy-5 (6)-TAMRA, a cyanine 555™ aminooxy, a cyanine 647™ aminooxy, an aminooxy-Alexa Fluor™ dye, such as Alexa Fluor™ 488 or Alexa Fluor™ 647, an aminooxy-biotin, a naphthalene-containing aminooxy-fluorescent dye, a guanidine-containing aminooxy-fluorescent dye, a naphthalene- and/or guanidine-containing aminooxy-FAM, a Cy™5-PEG-aminooxy, or a fluorescent dye hydrazide such as a cyanine dye hydrazide or a CF™ dye hydrazide.

In at least an embodiment of the present disclosure, the nucleic acid comprises a 5'-end nucleobase selected from the group consisting of hypoxanthine, cytosine, 3-alkyladenine, 8-oxoguanine (8-oxoG), uracil, 5-hydroxyuracil, 5-hydroxymethyluracil, 5-formyluracil, 5-fluorouracil, dihydroxyuracil, 5-formylcytosine, 5-carboxylcytosine, 3-methyladenine (3-meA), 3-methylguanine, 7-methyladenine, 7-methylguanine, N6-methyladenine, 8-oxo-7,8-dihydroguanine, 5-hydroxylcytosine, ethenocytosine, ethenoadenine, thymine glycol, cytosine glycol, 2,6-diamino-4-hydroxy-5-N-methylformamidopyrimidine, a formamidopyrimidine derivative of adenine, and a formamidopyrimidine derivative of guanine.

In some embodiments, the 5'-end glycosylase of the present disclosure may be a mono-functional DNA glycosylase. In at least an embodiment of the present disclosure, the mono-functional DNA glycosylase may be selected from the group consisting of uracil-DNA glycosylase (UDG or UNG), alkyladenine DNA glycosylase (AAG; also referred to as methylpurine DNA glycosylase (MPG)), single-strandselective monofunctional uracil-DNA glycosylase 1 (SMUG1), methyl-binding domain glycosylase 4 (MBD4), thymine DNA glycosylase (TDG), MutY homolog DNA glycosylase (MYH), alkylpurine glycosylase C (AlkC), alkylpurine glycosylase D (AlkD), 8-oxo-guanine glycosylase 1 (OGG1) without an abasic site lyase activity, endonuclease III-like glycosylase 1 (NTHL1) without the abasic site lyase activity, endonuclease VIII-like glycosylase 1 (NEIL1) without the abasic site lyase activity, endonuclease VIII-like glycosylase 2 (NEIL2) without the abasic site lyase activity, endonuclease VIII-like glycosylase 3 (NEIL3) without the abasic site lyase activity, enzymatically active fragments thereof and any combination thereof.

In at least an embodiment of the present disclosure, the uracil-DNA glycosylase is derived from the family of Micrococcaceae, Staphylococcaceae, or Caryophanaceae, which includes a genus of *Micrococcus, Stomatococcus, Staphylococci,* or *Planococcus*. In some embodiments, the uracil-DNA glycosylase is derived from *Micrococcus luteus*.

In at least an embodiment of the present disclosure, the detectable label is selected from the group consisting of an azide, an alkyne, a bicyclononyne (BCN), a dibenzocyclooctyne (DBCO), a maleimide, a peptide, a protein, an antibody, a dendrimer, a biotin, a radioisotope, a photochromic dye, a fluorescent dye, a luminescent dye, and any combination thereof.

In some embodiments, the method of the present disclosure further comprises providing a 5' to 3' exonuclease to remove unlabeled nucleic acids. In at least an embodiment, the 5' to 3' exonuclease is selected from the group consisting of T5 exonuclease (T5 exo), T7 exonuclease (T7 exo), bacterial alkaline exonuclease, viral alkaline exonuclease, phage lambda exonuclease, 5'-exonuclease of DNA polymerase I (ExoVI) from, e.g., *Streptococcus pneumoniae* or *Helicobacter pylori, Escherichia coli* exonuclease VIII (Exo VIII), RecJ from, e.g., *Escherichia coli* or Deinococcus radiodurans, RecJf derived from RecJ fusion to the maltose-binding protein, *Thermus thermophilus* (Tth) RecJ, *Mycoplasma pneumonia* (Mpn) NrnA, human exonuclease 5 (hEXO5), human exonuclease 1 (hEXO1), SNM1 from *Saccharomyces cerevisiae*, human or bovine SNM1A, human SNM1B/Apollo, bovine SNM1B, SXT-Exo from, e.g., *Vibrio cholerae*, phospholipase D3 (PLD3), phospholipase D4 (PLD4), Sso1391-Csa1 from, e.g., *Sulfolobus solfataricus*, Sto0027-Csa1 from, e.g., *Sulfolobus tokadaii*, Ttx1248-Csa1 from, e.g., *Thermoproteus tenax*, Sso1451-Csa1 from, e.g., *Sulfolobus solfataricus*, Sto2633-Csa1 from, e.g., *Sulfolobus tokadaii*, Pfu1793-Cas4 from, e.g., *Pyrococcus furiosus*, Sto2501 from, e.g., *Sulfolobus tokadaii*, Sso0001 from, e.g., *Sulfolobus solfataricus*, Sto2331-Cas4 from, e.g., *Sulfolobus tokadaii*, Ttx1245-Cas4 from, e.g., *Thermoproteus tenax*, Sso1449-Cas4 from, e.g., *Sulfolobus solfataricus*, Sto2635-Cas4 from, e.g., *Sulfolobus tokadaii*, Sso1392-Cas4 from, e.g., *Sulfolobus solfataricus, Sulfolobus islandicus* rod-shaped virus 2 (SIRV2) gp19, bacterial AddB, and any combination thereof.

In some embodiments, the method of the present disclosure further comprises a nucleic acid synthesis process to obtain a unique 5'-end nucleobase. In some embodiments, the nucleic acid having a unique 5'-end nucleobase is synthesized by a process well known in the art, including the phosphoramidite-based nucleic acid synthesis process, and the template-dependent and template-independent enzymatic nucleic acid synthesis processes.

In some embodiments, the method of the present disclosure further comprises isolating a nucleic acid fragment from a sample. For example, the nucleic acid may be isolated from a sample of intact or disrupted viruses or cells, such as bacterial, archaeal, and eukaryotic cells, e.g., human cells. Suitable samples include isolated cell and tissue samples, such as biopsies, including the solid tissue or tumor biopsies. In some embodiments, the sample may be obtained from a formalin-fixed paraffin embedded (FFPE) tissue sample or other stored samples of cellular materials.

The present disclosure also provides a kit for 5'-end labeling of a nucleic acid, and the kit comprises a 5'-end glycosylase and an aldehyde-reactive compound.

In some embodiments, the 5'-end glycosylase in the kit of the present disclosure is selected from the group consisting of uracil-DNA glycosylase (UDG or UNG), alkyladenine DNA glycosylase (AAG; also referred to as methylpurine DNA glycosylase (MPG)), single-strand-selective monofunctional uracil-DNA glycosylase 1 (SMUG1), methyl-binding domain glycosylase 4 (MBD4), thymine DNA glycosylase (TDG), MutY homolog DNA glycosylase (MYH), alkylpurine glycosylase C (AlkC), alkylpurine glycosylase D (AlkD), 8-oxo-guanine glycosylase 1 (OGG1) without an abasic site lyase activity, endonuclease III-like glycosylase 1 (NTHL1) without the abasic site lyase activity, endonuclease VIII-like glycosylase 1 (NEIL1) without the abasic site lyase activity, endonuclease VIII-like glycosylase 2 (NEIL2) without the abasic site lyase activity, endonuclease VIII-like glycosylase 3 (NEIL3) without the abasic site lyase activity, enzymatically active fragments thereof and any combination thereof.

In at least an embodiment, the uracil-DNA glycosylase in the kit of the present disclosure is derived from the family of Micrococcaceae, Staphylococcaceae, or Caryophanaceae, which includes a genus of *Micrococcus, Stomatococcus, Staphylococci,* or *Planococcus*. In some embodiments, the uracil-DNA glycosylase is derived from *Micrococcus luteus*.

In at least an embodiment, the aldehyde-reactive compound in the kit of the present disclosure is a compound having at least one primary amine, a hydrazide, an acylhydrazide, a compound having an aminooxy (—ONH$_2$) group, and a compound having a naphthalene- and/or guanidine-containing aminooxy group. In some embodiments, the aldehyde-reactive compound is a hydroxylamine biotin, a fluorescent dye-hydroxylamine such as Alexa Fluor™ 488 hydroxylamine, an aldehyde-reactive probe (ARP), an aminooxy-fluorescent dye such as an aminooxy-5 (6)-FAM, an aminooxy-hexachloro-fluorescein (HEX), an aminooxy-5 (6)-ROX and an aminooxy-5 (6)-TAMRA, a cyanine 555™ aminooxy, a cyanine 647™ aminooxy, an aminooxy-Alexa™ Fluor dye, such as Alexa Fluor™ 488 or Alexa Fluor™ 647, an aminooxy-biotin, a naphthalene-containing aminooxy-fluorescent dye, a guanidine-containing aminooxy-fluorescent dye, a naphthalene- and/or guanidine-containing aminooxy-FAM, a Cy™5-PEG-aminooxy, or a fluorescent dye hydrazide such as a cyanine dye hydrazide or a fluorescent CF™ dye hydrazide.

In at least an embodiment, the kit of the present disclosure further comprises a 5' to 3' exonuclease for removing an unlabeled nucleic acid. In some embodiments, the 5' to 3' exonuclease is selected from the group consisting of T5 exonuclease, T7 exonuclease, phage lambda exonuclease, 5'-exonuclease of DNA polymerase I (ExoVI), exonuclease VIII (Exo VIII), RecJ, RecJf, Tth RecJ, Mpn NrnA, human EXO5 (hEXO5), human exonuclease 1 (hEXO1), SNM1, SNM1A, human SNM1B/Apollo, bovine SNM1B, SXT-Exo, phospholipase D3 (PLD3), phospholipase D4 (PLD4), Sso1391-Csa1, Sto0027-Csa1, Ttx1248-Csa1, Sso1451-Csa1, Sto2633-Csa1, Pfu1793-Cas4, Sto2501, Sso0001, Sto2331-Cas4, Ttx1245-Cas4, Sso1449-Cas4, Sto2635-Cas4, Sso1392-Cas4, SIRV2 gp19, bacterial AddB, and any combination thereof.

The present disclosure further provides a system for 5'-end labeling of a nucleic acid, the system comprising a reaction reservoir, chamber or vessel, a liquid handling/transferring device, a temperature control unit, and a time control unit, wherein the liquid handling/transferring device is configured to transfer a 5'-end glycosylase and an aldehyde-reactive compound to a nucleic acid in the reaction reservoir, chamber or vessel for a period of time at a defined temperature, which is controlled by the temperature control unit.

The present disclosure further provides a kit for 5'-end labeling of a nucleic acid, the kit comprising a 5'-end glycosylase and an aldehyde-reactive compound. In some embodiments, the kit further comprises a 5' to 3' exonuclease for removing an unlabeled nucleic acid, such as T5 exonuclease, T7 exonuclease, bacterial alkaline exonuclease, viral alkaline exonuclease, phage lambda exonuclease, 5'-exonuclease of DNA polymerase I (ExoVI), exonuclease VIII (Exo VIII), RecJ, RecJf, Tth RecJ, Mpn NrnA, human exonuclease 5 (hEXO5), human exonuclease 1 (hEXO1), SNM1, SNM1A, human SNM1B/Apollo, bovine SNM1B, SXT-Exo, phospholipase D3 (PLD3), phospholipase D4 (PLD4), Sso1391-Csa1, Sto0027-Csa1, Ttx1248-Csa1, Sso1451-Csa1, Sto2633-Csa1, Pfu1793-Cas4, Sto2501, Sso0001, Sto2331-Cas4, Ttx1245-Cas4, Sso1449-Cas4, Sto2635-Cas4, Sso1392-Cas4, SIRV2 gp19, bacterial AddB, and any combination thereof.

In at least an embodiment, the 5'-end glycosylase is selected from the group consisting of uracil-DNA glycosylase (UDG or UNG), alkyladenine DNA glycosylase (AAG), single-strand-selective monofunctional uracil-DNA glycosylase 1 (SMUG1), methyl-binding domain glycosylase 4 (MBD4), thymine DNA glycosylase (TDG), MutY homolog DNA glycosylase (MYH), alkylpurine glycosylase C (AlkC), alkylpurine glycosylase D (AlkD), 8-oxo-guanine glycosylase 1 (OGG1) without an abasic site lyase activity, endonuclease III-like glycosylase 1 (NTHL1) without the abasic site lyase activity, endonuclease VIII-like glycosylase 1 (NEIL1) without the abasic site lyase activity, endonuclease VIII-like glycosylase 2 (NEIL2) without the abasic site lyase activity, endonuclease VIII-like glycosylase 3 (NEIL3) without the abasic site lyase activity, enzymatically active fragments thereof and any combination thereof. In at least an embodiment, the uracil-DNA glycosylase is derived from a family of Micrococcaceae, Staphylococcaceae, or Caryophanaceae. In at least an embodiment, the aldehyde-reactive compound is a hydroxylamine biotin, a fluorescent dye-hydroxylamine, an aldehyde-reactive probe (ARP), such as N-(aminooxyacetyl)-N'-biotinylhydrazine, an aminooxy-fluorescent dye, such as aminooxy-PEG-TAMRA (5-carboxytetramethylrhodamine), aminooxy-PEG-Cy™3 (Cyanine 3) dye, aminooxy-PEG-Cy™5 (Cyanine 5) dye, aminooxy-PEG-FAM (fluorescein amidite) dye, an aminooxy-poly(ethylene glycol)-azide (aminooxy-PEG-azide), an propargyl, an aminooxy-poly(ethylene glycol)-dibenzylcyclooctyne (aminooxy-PEG-DBCO), an aminooxy-poly(ethylene glycol)-bicyclononyne (BCN), a cyanine 555™ aminooxy, a cyanine 647™ aminooxy, an aminooxy-Alexa Fluor™ dye, such as Alexa Fluor™ 488 or Alexa Fluor™ 647, an aminooxy-biotin, a naphthalene-containing aminooxy-fluorescent dye, a guanidine-containing aminooxy-fluorescent dye, a fluorescent dye hydrazide, or a maleimide.

BRIEF DESCRIPTION OF THE DRAWINGS

The present disclosure can be more understood by reading the following descriptions of the embodiments, with reference made to one or more of the accompanying drawings below.

DETAILED DESCRIPTION

Figure 1:
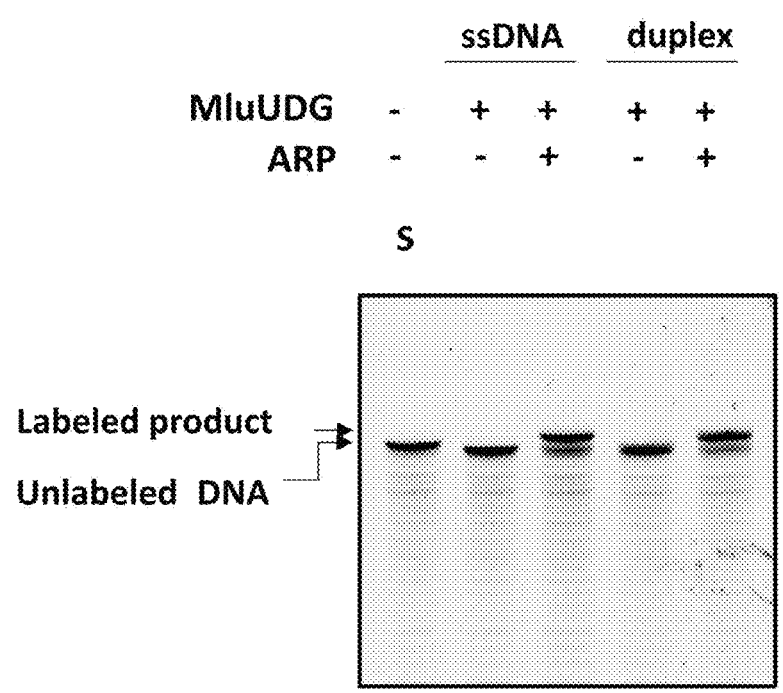
FIG. 1 shows the urea-PAGE result of 5'-end labeling on a single-stranded DNA (ssDNA) and a duplex DNA with a uracil-DNA glycosylase derived from *Micrococcus luteus* (MluUDG) and an aldehyde-reactive probe (ARP). "S" denotes the lane containing only unlabeled DNA.

The following examples are used for illustrating the present disclosure. A person skilled in the art can easily conceive the other effects of the present disclosure, based on the disclosure of the specification. It will be apparent that one or more embodiments may be practiced without specific details. The present disclosure can also be implemented or applied as described in different examples. It is possible to modify or alter the following examples for carrying out this disclosure without contravening its scope for different applications. Titles or subtitles may be used in this disclosure for the convenience of a reader, which shall have no influence on the scope of the present disclosure.

In this disclosure, all terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the descriptions of the present disclosure. Thus, the terms used herein are defined based on the meaning of the terms together with the descriptions throughout the specification.

The practice of the present disclosure employs, unless otherwise indicated, conventional techniques of molecular biology, microbiology, cell biology, and biochemistry, which are well within the purview of a skilled artisan in the art. Such techniques are explained fully in the literature, such as "Molecular Cloning: A Laboratory Manual," second edition (Sambrook, et al., 1989), Cold Spring Harbor Press; "Oligonucleotide Synthesis" (M. J. Gait, 1984); "Methods in Molecular Biology," Humana Press; "Cell Biology: A Laboratory Notebook" (J. E. Cellis, ed., 1998) Academic Press; "Animal Cell Culture" (R. I. Freshney, ed., 1987); "Introduction to Cell and Tissue Culture" (J. P. Mather and P. E. Roberts, 1998); "Cell and Tissue Culture: Laboratory Procedures" (A. Doyle, J. B. Griffiths, and D. G. Newell, eds., 1993-8); "Methods in Enzymology" (Academic Press, Inc.); "Gene Transfer Vectors for Mammalian Cells" (J. M. Miller and M. P. Calos, 1987); "Current Protocols in Molecular Biology" (F. M. Ausubel, et al., eds., 1987); "PCR: The Polymerase Chain Reaction (Mullis, et al., eds., 1994); "Short Protocols in Molecular Biology" (Wiley and Sons, 1999). Particularly useful techniques for particular embodiments will be discussed in the sections that follow. Without further elaboration, it is believed that one skilled in the art can, based on the above descriptions, utilize the present disclosure to its fullest extent. The following embodiments are, therefore, to be construed as merely illustrative, and not limitative of the remainder of the disclosure in any way whatsoever. All publications cited herein are incorporated by reference for the purposes or subject matter referenced herein.

As used in this disclosure, the singular forms "a," "an," and "the" include plural referents unless expressly and unequivocally limited to one referent. The term "or" is used interchangeably with the term "and/or" unless the context clearly indicates otherwise.

Also, when a part "includes" or "comprises" a component or a step, unless there is a particular description contrary thereto, the part can further include other components or other steps, not excluding the others.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of this disclosure, unless the context clearly dictates otherwise.

As used herein, the terms "about," "approximately," and "around" generally mean within 10%, 5%, 1%, or 0.5% of a given value or range. Alternatively, the terms "about," "approximately," and "around" mean within an acceptable standard error of the mean when considered by one of ordinary skill in the art. Unless otherwise expressly specified, all of the numerical ranges, amounts, values, and percentages such as those for quantities of materials, durations of time periods, temperatures, operating conditions, ratios of amounts, and the likes disclosed herein should be understood as modified in all instances by the terms "about," "approximately" or "around."

As used herein, the term "derived," when referring to a biological sample, indicates the sample being obtained from the stated source at some point in time. For example, a biological sample derived from an organism can represent a primary biological sample obtained directly from the organism (i.e., unmodified), or can be modified, e.g., by introduction of a recombinant vector, by culturing under particular conditions, or immortalization.

As used herein, the phrase "at least one," in reference to a list of one or more elements, should be understood to mean at least one element selected from any one or more of the elements in the list of elements, but not necessarily including at least one of each and every element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, an abasic site, also known as an apurinic/apyrimidinic (AP) site, encompasses any chemical structure following removal of a base portion (including the entire base) with an agent capable of cleaving a base portion of a nucleotide, e.g., by the treatment of a nucleotide (present in a polynucleotide chain) with an agent (e.g., an enzyme, acidic conditions, or a chemical reagent) capable of effecting cleavage of a base portion of a nucleotide. In an embodiment, an AP site is a position in the backbone of nucleic acids such as deoxyribonucleic acids (DNAs) or ribonucleic acids (RNAs) that lacks a nucleobase, i.e., a deoxyribose of the DNA backbone or a ribose of the RNA backbone not covalently linked to either a purine base, such as adenine (A) or guanine (G), or a pyrimidine base, such as cytosine (C), uracil (U) or thymine (T). An AP site may be internal within the nucleotide sequence of the nucleic acids at both 5' and 3' ends of the nucleic acids, or at one end of the nucleic acids, such as the 5' end or the 3' end.

The nucleic acids as used herein may be single-stranded, double-stranded, or a mixture of single- and double-stranded nucleic acids. The double-stranded nucleic acids may be nucleic acids having at least a region of duplex formed by two complementary strands of nucleic acids. For example, the nucleic acids are DNA molecules, such as plasmids, synthetic DNAs, or viral DNAs. In other embodiments, the nucleic acids may be RNA molecules, such as synthetic RNAs, mRNAs, tRNAs, rRNAs, and non-coding RNAs. The term also includes analogs of either DNA or RNA made from nucleotide analogs, and as applicable, single-(sense or antisense) and double-stranded polynucleotides. The term further includes modified polynucleotides, including modified DNAs and modified RNAs, e.g., DNA and RNA comprising one or more unnatural nucleotides or nucleosides. The terms "nucleic acids" and "polynucleotides" may be used interchangeably herein to refer to deoxyribonucleotides or ribonucleotides and polymers thereof in either single- or double-stranded form. These terms encompass nucleic acids containing known nucleotide analogs or modified backbone residues or linkages, which are synthetic, naturally occurring, and non-naturally occurring, and/or which have similar chemical properties as the reference nucleic acids, and/or which are metabolized in a manner similar to the reference nucleotides. Unless otherwise indicated, a particular nucleic acid sequence also encompasses conservatively modified variants thereof (e.g., degenerate codon substitutions) and complementary sequences, as well as the sequence explicitly indicated. In some embodiments, nucleotides are linked via internucleotide linkages such as, but not limited to, phosphate, boranephosphate, phosphorothioate, phosphodiester, phosphotriester, H-phosphonate, aminophosphonate, methylphosphonate, phosphonoacetate, sulfur phosphonoacetate, or other variants of the phosphate backbone of natural nucleic acids. The term "nucleotide" as used herein also encompasses structural analogs in place of natural or non-natural nucleotides, such as modified nucleotides. For example, the term "xeno nucleotide" refers to the nucleotide being modified to have a different sugar moiety than those contained in a natural DNA or RNA. The exemplary nucleic acids having the xeno nucleotide, i.e., xeno-nucleic acids (XNAs), include, but are not limited to, peptide nucleic acid (PNA), locked nucleic acid (LNA), 1,5-anhydrohexitol nucleic acid (HNA), threose nucleic acid (TNA), glycol nucleic acid (GNA), cyclohexene nucleic acid (CeNA), and fluoro-arabino nucleic acid (FANA).

The nucleic acids as used herein may be 5 bases to 10,000 bases in length, such as 10 to 3,000 bases in length, 10 to 1,000 bases in length, or 10 to 100 bases in length. The nucleic acids isolated from biological sources may be greater than 1,000 bases in length and may be fragmented, for example, by sonication, for use as described herein.

In some embodiments, the nucleic acids to be labeled by the method of the present disclosure can be about 10, about 15, about 20, about 25, about 30, about 35, about 40, about 50, about 65, about 75, about 85, about 100, about 125, about 150, about 175, about 200, about 225, about 250, about 300, about 350, about 400, about 450, about 500, about 550, about 600, about 650, or more nucleotides in length. In some embodiments, said nucleic acids can be at least about 5, about 6, about 7, about 8, about 9, about 10, about 15, about 20, about 25, about 30, about 35, about 40, about 50, about 65, about 75, about 85, about 100, about 125, about 150, about 175, about 200, about 225, about 250, about 300, about 350, about 400, about 450, about 500, about 550, about 600, about 650 or more nucleotides in length. In other embodiments, said nucleic acids can be less than about 20, about 25, about 30, about 35, about 40, about 50, about 65, about 75, about 85, about 100, about 125, about 150, about 175, about 200, about 225, about 250, about 300, about 350, about 400, about 450, about 500, about 550, about 600, or about 650 nucleotides in length. It is understood that the lengths of nucleic acids may represent an average size in the population.

As used herein, a glycosylase is an enzyme capable of excising a base portion of a nucleotide and creating an AP site in a nucleic acid, which includes N-glycosylases and is also called as "DNA glycosylase" or "glycosidase," including, but not limited to, uracil N-glycosylase (UNG) that specifically cleaves dUTP and is interchangeably termed as "uracil DNA glycosylase" (UDG); hypoxanthine-N-glycosylase; hydroxymethyl cytosine-N-glycosylase; 3-methyladenine DNA glycosylase; 3- or 7-methylguanine DNA glycosylase; hydroxymethyl uracil DNA glycosylase; and T4 endonuclease V. A glycosylase cleaves a base portion of the nucleotide in the middle, or at either or both ends of a nucleic acid. As used herein, a 5'-end glycosylase excises a base portion of the nucleotide at the 5'-end of a nucleic acid.

As used herein, the term "exonuclease" refers to any wild-type or variant enzyme, which is capable of cleaving phosphodiester bond(s) linking the end nucleotides of an oligonucleotide or a polynucleotide, such as a 5' to 3' exonuclease, a 3' to 5' exonuclease, and a poly(A)-specific 3' to 5' exonuclease. Non-limiting examples of exonucleases include exonuclease I, exonuclease II, exonuclease III, exonuclease IV, exonuclease V, exonuclease VI, exonuclease VII, exonuclease VIII, Xm1, and Rat1.

As used herein, the term "5' to 3' exonuclease" refers to an exonuclease that breaks phosphodiester bonds at the 5' end of an oligonucleotide or a polynucleotide. Non-limiting examples of 5' to 3' exonucleases include T5 exonuclease, T7 exonuclease, bacterial alkaline exonuclease, viral alkaline exonuclease, phage lambda exonuclease, 5'-exonuclease of DNA polymerase I, exonuclease VIII, RecJ, RecJf, Tth RecJ, Mpn NrnA, human exonuclease 5, human exonuclease 1, SNM1, SNM1A, human SNM1B/Apollo, bovine SNM1B, SXT-Exo, phospholipase D3, phospholipase D4, Sso1391-Csa1, Sto0027-Csa1, Ttx1248-Csa1, Sso1451-Csa1, Sto2633-Csa1, Pfu1793-Cas4, Sto2501, Sso0001, Sto2331-Cas4, Ttx1245-Cas4, Sso1449-Cas4, Sto2635-Cas4, Sso1392-Cas4, SIRV2 gp19, and bacterial AddB.

As used herein, the term "3'-end" generally refers to a region or position in a polynucleotide or oligonucleotide downstream from the 5'-region or position in the same polynucleotide or oligonucleotide.

As used herein, the term "5'-end" generally refers to a region or position in a polynucleotide or oligonucleotide upstream from the 3'-region or position in the same polynucleotide or oligonucleotide.

As used herein, an aldehyde-reactive compound is a class of compounds that reacts to or forms a bond with an aldehyde group. In an embodiment, an aldehyde-reactive compound structurally is a compound having at least one primary amine, a hydrazide, an acylhydrazide, a compound having an aminooxy ($-ONH_2$) group, a compound having a naphthalene-containing aminooxy group and/or a guanidine-containing aminooxy group.

As used herein, the term "label" (interchangeably called a "detectable label" or "modification") refers to a chemical group or a functional moiety that is associated or linked with a polynucleotide (interchangeably called "labeling" or "modified"). The labeled polynucleotide may be directly or indirectly detected, generally through a detectable signal. The detectable label can be attached (or associated) either directly or through a non-interfering linkage group with other moieties capable of specifically associating with one or more sites to be labeled. The detectable label may be covalently or non-covalently associated as well as directly or indirectly associated.

As used herein, the term "mono-functional DNA glycosylase" refers to a naturally existing mono-functional glycosylase that intrinsically contains only a DNA glycosylase activity. The term "mono-functional DNA glycosylase" may also refer to a mono-functional glycosylase that is derived from a bi-functional DNA glycosylase naturally having both DNA glycosylase and abasic-site lyase (AP lyase) activities by eliminating or inactivating the AP lyase domain of the bi-functional DNA glycosylase.

As used herein, the term "enzymatically active fragment" refers to a fragment of a catalytically or enzymatically active protein or polypeptide which contains at least 10%, e.g., at least 20%, at least 30%, at least 40%, at least 50%, at least 60%, at least 70%, at least 80%, at least 90%, or at least 95% of activity of the protein or polypeptide from which the fragment is derived.

The processes of signal detection are known in the art. Signal detection may be visual or utilize a suitable instrument appropriate for the label used, such as a spectrometer, fluorimeter, luminometer, phosphorimager, Geiger counter, scintillation counter, or microscope. For example, where the label is a radioisotope, detection can be achieved using, for example, a scintillation counter or a photographic film as in autoradiography. Where a fluorescent label is used, detection may be achieved by exciting the fluorochrome with an appropriate wavelength of light and detecting the emitting fluorescence, such as by a fluorescence microscopy, visual inspection, photographic film, fluorometer, luminometer, charge-coupled device (CCD) cameras, and scanner. Where enzymatic labels are used, detection may be achieved by providing appropriate substrates for the enzyme and detecting the resulting reaction product. For example, many substrates of horseradish peroxidase, such as o-phenylenediamine, give colored products. Instruments suitable for high sensitivity detection are known in the art. Otherwise, the signal amplification strategies can be optionally used to facilitate the detection of low-abundance molecular targets.

The kits provided herein are in suitable packaging. Suitable packaging includes, but is not limited to, vials, bottles, jars, flexible packaging, and the like. Also contemplated are packages for use in combination with a device or a system. The kits optionally may include additional components such as buffers and interpretive information. In some embodiments, the disclosure provides articles of manufacture comprising contents of the kits described herein.

EXAMPLES

Exemplary embodiments of the present disclosure are further described in the following examples, which should not be construed to limit the scope of the present disclosure. The materials and methods used in the following Examples are described in detail below. The materials used in the present disclosure but unannotated herein are commercially available.

Example 1. 5'-End Labeling of Nucleic Acids Using an Aldehyde-Reactive Compound

A 45-mer single-stranded DNA (ssDNA; 5'-/deoxyU/CTCGGCCTGGCACAGGTCCGT-CTCAGTGCTGCGGCGACCACCGA-3' (SEQ ID NO: 1)) containing a uracil residue at the 5'-end and a fluorescein (FAM) dye at the 3'-end was synthesized. To carry out the uracil excision and subsequent abasic site labeling, 100 nM of 45-mer uracil-containing ssDNA was mixed with 100 ng of uracil-DNA glycosylase derived from *Micrococcus luteus* (MluUDG) and 5 mM of an aldehyde-reactive probe (N-(aminooxyacetyl)-N'-biotinylhydrazine). The reaction was initiated by the addition of MluUDG and the aldehyde-reactive probe (ARP) at 37° C. for 15 minutes. The reaction was terminated by adding an equal volume of 2× quench solution (30 mM EDTA and 95% (v/v) de-ionized formamide) and then denatured at 95° C. for 10 min. The reaction products were analyzed by a denaturing 20% polyacrylamide gel electrophoresis containing 8 M urea (urea-PAGE). The result was visualized by scanning the gel at Amersham Typhoon Imager (Cytiva Life Sciences, Marlborough, MA, USA) and shown in FIG. 1. As shown in FIG. 1, the addition of MluUDG and the aldehyde-reactive probe produced an additional band with a higher molecular weight in the gel image, indicating the presence of a labeled ssDNA product.

Similarly, in another example, a partial duplex DNA molecule was labeled with an aldehyde-reactive probe and analyzed. The duplex DNA was prepared by annealing the 45-mer uracil-containing ssDNA (SEQ ID NO: 1) to a 15-mer complementary strand (5'-TGTGCCAGGCCGAGA-3' (SEQ ID NO: 2)) at a molar ratio of 1:1.5 in the 1×Tris-EDTA (TE) buffer consisting of 10 mM Tris-HCl (pH 8.0), 1 mM EDTA, and 100 mM NaCl. The DNA annealing reaction was performed in a thermal cycler by heating up the DNA mixture to 98° C. for 3 minutes, followed by gradually cooling down (e.g., 30 seconds for every 5° C.) to 4° C. The resulting duplex DNA was subjected to the uracil excision by MluUDG and subsequent abasic site labeling as described in the above steps and conditions for labeling ssDNA. The reaction was terminated by adding an equal volume of 2× quench solution and then denatured at 95° C. for 10 min. The reaction products were analyzed by a 20% urea-PAGE. The result was visualized by scanning the gel at Amersham Typhoon Imager and shown in FIG. 1. In FIG. 1, the addition of MluUDG and the aldehyde-reactive probe to the duplex DNA generated an additional band with a higher molecular weight in the gel, indicating the presence of a labeled DNA product.

Therefore, both the single-stranded and duplex DNAs were able to be labeled with an aldehyde-reactive probe by the provided method.

Example 2. 5'-End Labeling of Nucleic Acids Using an Aminooxy-5(6)-FAM

Figure 2:
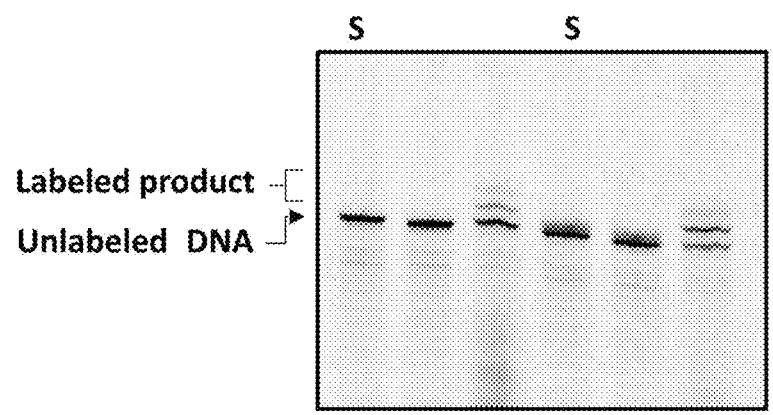
FIG. 2 shows the urea-PAGE result of 5'-end labeling on a single stranded DNA and a duplex DNA with a uracil-DNA glycosylase derived from *Micrococcus luteus* (MluUDG) and an aminooxy-5(6)-FAM. "S" denotes the lane containing only unlabeled DNA.

A 45-mer single-stranded DNA (ssDNA; SEQ ID NO: 1) containing a uracil residue at the 5'-end and a Cyanine 5 (Cy™5) dye at the 3'-end was synthesized. To carry out the uracil excision and subsequent abasic site labeling, 100 nM of the ssDNA was mixed with 100 ng of uracil-DNA glycosylase derived from *Micrococcus luteus* (MluUDG) and 2 mM of aminooxy-5 (6)-FAM. The reaction was initiated by the addition of MluUDG and aminooxy-5 (6)-FAM and incubated at 37° C. for 60 minutes. The reaction was terminated by adding an equal volume of 2x quench solution (30 mM EDTA and 95% (v/v) de-ionized formamide) and then denatured at 95° C. for 10 min. The reaction products were analyzed by a 20% urea-PAGE. The result was visualized by scanning the gel at Amersham Typhoon Imager. As shown in FIG. 2, the addition of MluUDG and the aminooxy-5 (6)-FAM produced additional bands with higher molecular weights in the gel, indicating the presence of labeled FAM-ssDNA products.

Likewise, in another example, a partial duplex DNA molecule was labeled with an aminooxy-5(6)-FAM and analyzed. The duplex DNA was prepared by annealing the 45-mer uracil-containing ssDNA (SEQ ID NO: 1) to a 15-mer complementary strand (5'-TGTGCCAGGCCGAGA-3' (SEQ ID NO: 2)) at a molar ratio of 1:1.5 in the 1×TE buffer consisting of 10 mM Tris-HCl (pH 8.0), 1 mM EDTA, and 100 mM NaCl. The DNA annealing reaction was performed in a thermal cycler by heating up the DNA mixture to 98° C. for 3 minutes and gradually cooling down (e.g., 30 seconds for every 5° C.) to 4° C. The resulting duplex DNA was subjected to the uracil excision by MluUDG and subsequent abasic site labeling as described in the above steps and conditions for labeling ssDNA. The reaction was terminated, and the reaction products were analyzed by a 20% urea-PAGE. The result was visualized by scanning the gel at Amersham Typhoon Imager. As also shown in FIG. 2, the addition of MluUDG and the aminooxy-5(6)-FAM to the duplex DNA generated additional bands with higher molecular weights in the gel, indicating the presence of labeled FAM-DNA products.

Hence, both single-stranded and duplex DNAs were shown to be labeled with the aminooxy-5(6)-FAM by the provided method.

Figure 3:
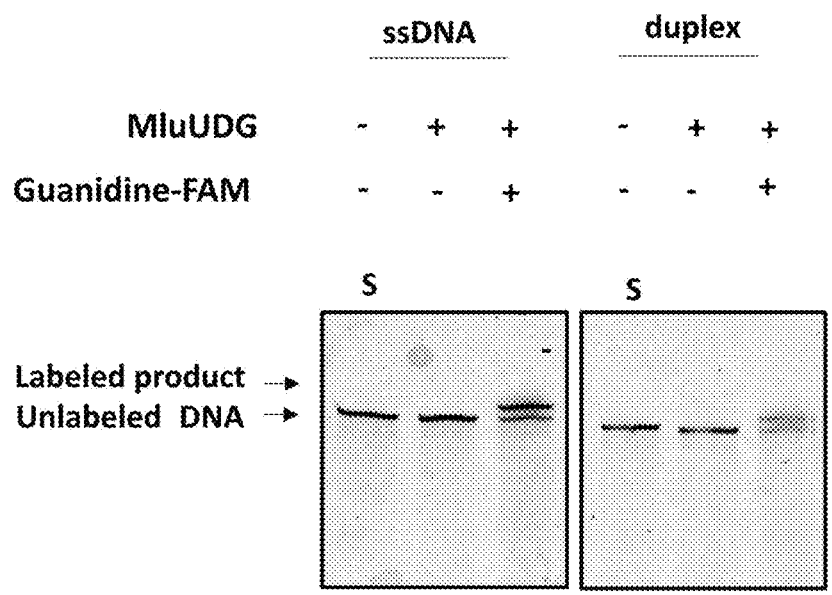
FIG. 3 shows the urea-PAGE result of 5'-end labeling on a 5'-phosphorylated single-stranded DNA and a duplex DNA with a uracil-DNA glycosylase derived from *Micrococcus luteus* (MluUDG) and a naphthalene- and guanidine-containing aminooxy-FAM (Guanidine-FAM). "S" denotes the lane containing only unlabeled DNA.

Example 3. 5'-End Labeling of DNA with the Naphthalene- and Guanidine-Containing Aminooxy-FAM A 47-mer single-stranded DNA (ssDNA; 5'-/deoxyU/CTCGGCCTGGCACAGGTCCG-TCTCAGTGCTGCGGCGACCACCGAGG-3'(SEQ ID NO: 3)) containing a uracil residue at the 5'-end was synthesized. To carry out the uracil excision and subsequent abasic site labeling, 100 nM of the ssDNA was mixed with 100 ng of uracil-DNA glycosylase derived from *Micrococcus luteus* (MluUDG) and 2 mM of naphthalene- and guanidine-containing aminooxy-FAM. The reaction was initiated by the addition of MluUDG and a naphthalene- and guanidine-containing aminooxy-FAM and incubated at 37° C. for 60 minutes. The reaction was terminated by adding an equal volume of 2x quench solution (30 mM EDTA and 95% (v/v) de-ionized formamide) and then denatured at 95° C. for 10 min. The reaction products were analyzed by a 20% urea-PAGE. The result was visualized by scanning the gel at Amersham Typhoon Imager. As shown in FIG. 3, the addition of MluUDG and the naphthalene- and guanidine-containing aminooxy-FAM generated an additional band with a higher molecular weight in the gel, indicating the presence of a labeled FAM-ssDNA product.

Similarly, in another example, a partial duplex DNA molecule was also labeled with the naphthalene- and guanidine-containing aminooxy-FAM and analyzed. The duplex DNA was prepared by annealing the 47-mer uracil-containing ssDNA (SEQ ID NO: 3) to a 15-mer complementary strand (SEQ ID NO: 2) at a molar ratio of 1:1.5 in the 1×TE buffer consisting of 10 mM Tris-HCl (pH 8.0), 1 mM EDTA, and 100 mM NaCl. The DNA annealing reaction was performed in a thermal cycler by heating up the DNA mixture to 98° C. for 3 minutes and gradually cooling down (e.g., 30 seconds for every 5° C.) to 4° C. The resulting duplex DNA was subjected to the uracil excision and subsequent abasic site labeling as described in the above steps and conditions for labeling ssDNA. The reaction was terminated, and the reaction products were analyzed by a 20% urea-PAGE. The result was visualized by scanning the gel at Amersham Typhoon Imager. As also shown in FIG. 3, the addition of MluUDG and the naphthalene- and guanidine-containing aminooxy-FAM to the duplex DNA generated an additional band with a higher molecular weight in the gel, indicating the presence of a FAM-labeled duplex DNA product.

Therefore, both single-stranded and duplex DNAs were able to be labeled with the naphthalene- and guanidine-containing aminooxy-FAM by the provided method.

Figure 4:
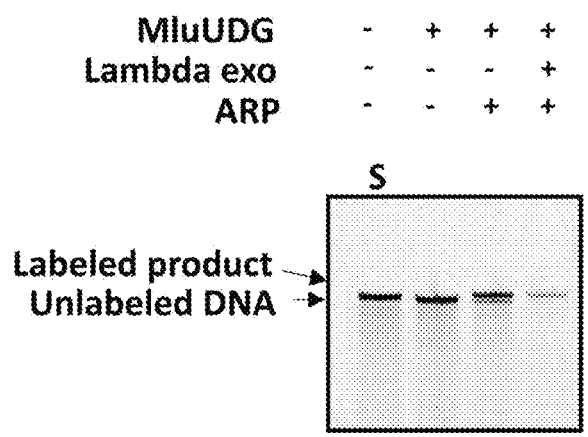
FIG. 4 shows the urea-PAGE result of 5'-end labeling on a single-stranded DNA with a uracil-DNA glycosylase derived from *Micrococcus luteus* (MluUDG) and an aldehyde-reactive probe (ARP) followed with a cleanup step to eliminate the unlabeled DNA using a phage lambda exonuclease (lambda exo). "S" denotes the lane containing only unlabeled DNA.

Example 4. 5'-End Labeling of 5'-Phosphorylated DNA with an Aldehyde-Reactive Compound and the Enrichment of Labeled DNA Using a Phage Lambda Exonuclease A 45-mer single-stranded DNA (ssDNA; SEQ ID NO: 1) containing a uracil residue at the 5'-end and a fluorescein (FAM) at the 3'-end was synthesized. The DNA was first 5'-end phosphorylated by T4 polynucleotide kinase in the presence of adenosine triphosphate (ATP) at 37° C. for 10 minutes. To carry out the uracil excision and subsequent abasic site labeling, 100 nM of 5'-phosphorylated ssDNA was mixed with 100 ng of uracil-DNA glycosylase derived from *Micrococcus luteus* (MluUDG) and 5 mM of aldehyde-reactive probe (N-(aminooxyacetyl)-N'-biotinylhydrazine). The reaction was initiated by the addition of MluUDG and the aldehyde-reactive probe at 37° C. simultaneously for 15 minutes. To eliminate the unlabeled ssDNA, 2 units of phage lambda exonuclease were added and then incubated at 37° C. for additional 3.5 hours. The reaction was stopped by adding an equal volume of 2x quench solution (30 mM EDTA and 95% (v/v) de-ionized formamide) and then denatured at 95° C. for 10 min. The reaction products were analyzed by a 20% urea-PAGE. The result was visualized by scanning the gel at Amersham Typhoon Imager. As shown in FIG. 4, the addition of MluUDG and the aldehyde-reactive probe generated an additional band with a higher molecular weight in the gel, indicating the presence of a labeled ssDNA product. When the reaction mixture was further treated with the phage lambda exonuclease to degrade the unlabeled DNA (i.e., a cleanup step), the portion of labeled ssDNA product was further enriched.

Therefore, DNAs can be labeled with an aldehyde-reactive probe by the provided method, and the labeled DNA fraction can be further enriched by the treatment with the phage lambda exonuclease.

Figure 5:
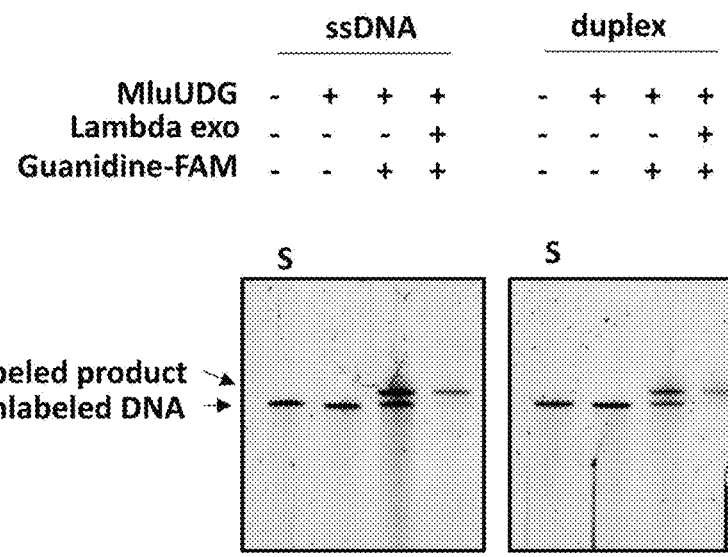
FIG. 5 shows the urea-PAGE result of 5'-end labeling on a single-stranded DNA and a duplex DNA with a uracil-DNA glycosylase derived from *Micrococcus luteus* (MluUDG) and a naphthalene- and guanidine-containing aminooxy-FAM (Guanidine-FAM) followed with a cleanup step to eliminate the unlabeled DNA using a phage lambda exonuclease (lambda exo). "S" denotes the lane containing only unlabeled DNA.

Example 5. 5'-End Labeling of 5'-Phosphorylated DNA with a Naphthalene- and Guanidine-Containing Aminooxy-FAM and the Purification and Enrichment of FAM-Labeled DNA Using Phage Lambda Exonuclease A 47-mer single-stranded DNA (ssDNA; SEQ ID NO: 3) containing a uracil residue at the 5'-end was synthesized. The DNA was first 5'-end phosphorylated by T4 polynucleotide kinase in the presence of adenosine triphosphate (ATP) at 37° C. for 30 minutes. To carry out the uracil excision and subsequent abasic site labeling, 100 nM of the ssDNA was mixed with 115 ng of uracil-DNA glycosylase derived from *Micrococcus luteus* (MluUDG) and 1 mM of naphthalene- and guanidine-containing aminooxy-FAM. The reaction was initiated by the addition of MluUDG and the naphthalene- and guanidine-containing aminooxy-FAM and incubated at 37° C. for 30 minutes. To eliminate the unlabeled ssDNA, 2 units of phage lambda exonuclease were added and then incubated at 37° C. for additional 30 minutes. The reaction was stopped by adding an equal volume of 2× quench solution (30 mM EDTA and 95% (v/v) de-ionized formamide) and then denatured at 95° C. for 10 min. The reaction products were analyzed by a 20% urea-PAGE. The result was visualized by scanning the gel at Amersham Typhoon Imager. As shown in FIG. 5, the addition of MluUDG and the naphthalene- and guanidine-containing aminooxy-FAM generated an additional band with a higher molecular weight in the gel, indicating the presence of a FAM-labeled ssDNA product. When the reaction mixture was further treated with the phage lambda exonuclease to degrade the unlabeled DNA, the FAM-labeled ssDNA product was enriched.

Similarly, in another example, a 5'-phophorylated duplex DNA molecule was also labeled with the naphthalene- and guanidine-containing aminooxy-FAM before subjected to the phage lambda exonuclease treatment to enrich the FAM-labeled duplex DNA. The duplex DNA was prepared by annealing the 47-mer uracil-containing ssDNA (SEQ ID NO: 3) to a 15-mer complementary strand (SEQ ID NO: 2) at a molar ratio of 1:1.5 in the 1×TE buffer consisting of 10 mM Tris-HCl (pH 8.0), 1 mM EDTA, and 100 mM NaCl. The DNA annealing reaction was performed in a thermal cycler by heating up the DNA mixture to 98° C. for 3 minutes and gradually cooling down (e.g., 30 seconds for every 5° C.) to 4° C. The resulting duplex DNA was first 5'-phosphorylated by T4 polynucleotide kinase in the presence of ATP and then subjected to the uracil excision and subsequent abasic site labeling followed with the phage lambda exonuclease treatment as described in the above steps and conditions for ssDNA labeling. The reaction product was analyzed by a 20% urea-PAGE. The result was visualized by scanning the gel at Amersham Typhoon Imager. As shown in FIG. 5, the addition of MluUDG and the naphthalene- and guanidine-containing aminooxy-FAM to the duplex DNA generated an additional band with a higher molecular weight in the gel, indicating the presence of a FAM-labeled DNA product. When the reaction mixture was further treated with the phage lambda exonuclease to degrade the unlabeled DNA, the FAM-labeled DNA product was enriched.

Therefore, both single-stranded and duplex DNAs can be labeled with the naphthalene- and guanidine-containing aminooxy-FAM by the provided method, and the labeled DNA fraction can be further enriched by the treatment with the phage lambda exonuclease.

Example 6. 5'-End Labeling of ssDNA with a Fluorescent Dye, a Biotin Moiety, an Azide, or a Dibenzylcyclooctyne (DBCO) Functional Group The 5'-end labeling, or modification at the 5'-end of a 45-mer single-stranded DNA (ssDNA; SEQ ID NO: 1) containing a uracil residue at the 5'-end, was carried out with 100 nM of ssDNA, 1 mM of uracil-DNA glycosylase, and 200 mM of the desiring molecule to be added to the 5'-end of the ssDNA, including aminooxy-polyethylene glycol (PEG)-TAMRA (5-carboxytetramethylrhodamine), aminooxy-PEG-Cy™3 (Cyanine 3) dye, aminooxy-PEG-Cy™5 (Cyanine 5) dye, aminooxy-PEG-FAM (fluorescein amidite) dye, ARP (aldehyde-reactive probe, N-(aminooxyacetyl)-N'-biotinylhydrazine), aminooxy-PEG-azide and aminooxy-PEG-dibenzylcyclooctyne (DBCO), in the reaction buffer containing 1 mM Tris-HCl (pH 8.0), 5 mM NaCl, 10 mM EDTA, and 0.02% PEG4000.

The DNA labeling reactions were incubated at 37° C. for 60 min and then stopped by the addition of an equal volume (10 mL) of 2× quench solution (30 mM EDTA and 95% deionized formamide). The reaction products of 5'-end labeling of ssDNA were analyzed by a 20% polyacrylamide gel electrophoresis (PAGE) containing 8 M urea. The gel was first stained with 1× SYBR Gold Nucleic Acid Gel Stain solution (Waltham, MA, U.S.A.) and visualized by scanning the gel at Amersham Typhoon Biomolecular Imagers (Marlborough, MA, U.S.A.).

Figure 6:
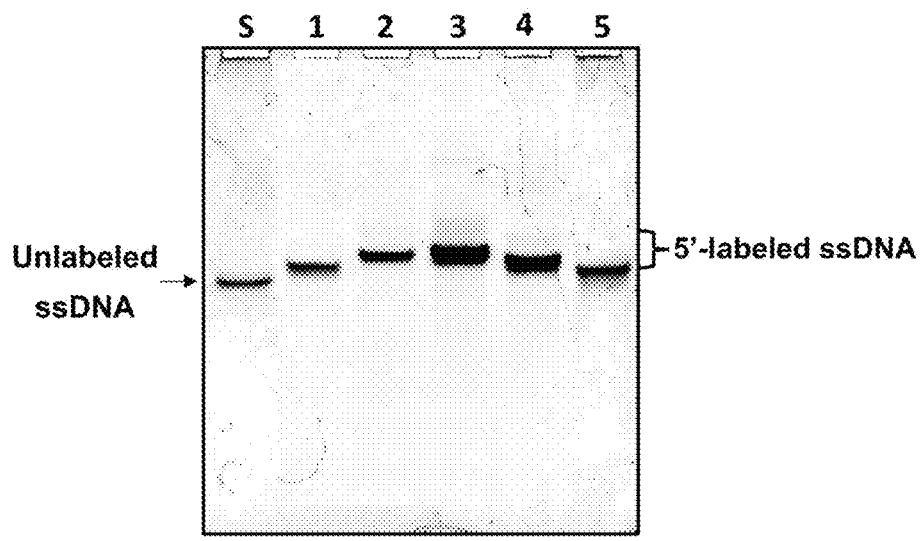
FIG. 6 shows the urea-PAGE result of 5'-end labeling on a single-stranded DNA (ssDNA) with a fluorescent dye or a biotin moiety. "S" denotes the lane containing unlabeled ssDNA. Lanes 1 to 4 show the ssDNA samples labeled with 5-TAMRA (5-carboxytetramethylrhodamine), Cy™3 (Cyanine 3) dye, Cy™5 (Cyanine 5) dye, and FAM (fluorescein) dye, respectively. Lane 5 shows the ssDNA labeled with a biotin moiety.

The results of 5'-end labeling of ssDNA with a fluorescent dye or a biotin moiety were shown in FIG. 6, where lane S shows the position of an unlabeled ssDNA, and lanes 1 to 5 show the higher electrophoretic positions of 5'-end labeled products of ssDNA, respectively, with 5-TAMRA (5-carboxytetramethylrhodamine), Cy™3 (Cyanine 3) dye, Cy™5 (Cyanine 5) dye, FAM (fluorescein) dye, and a biotin moiety (ARP).

Figure 7:
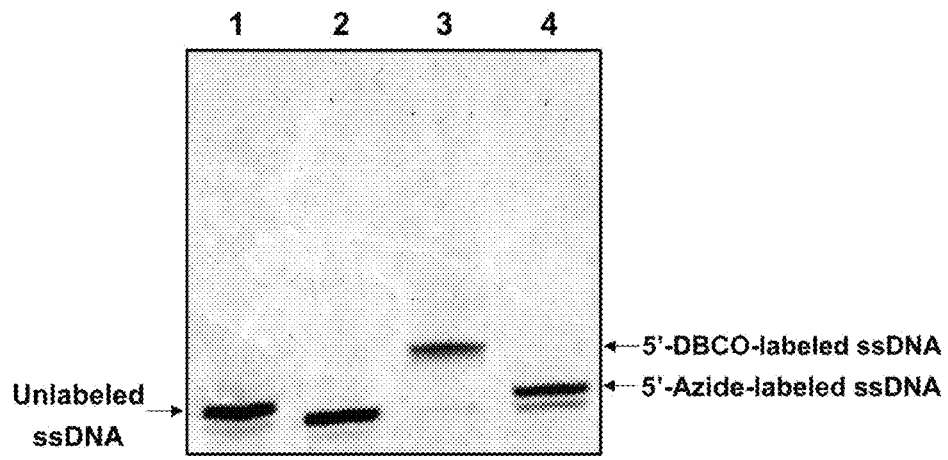
FIG. 7 shows the urea-PAGE result of 5'-end labeling on a single-stranded DNA (ssDNA) with a dibenzylcyclooctyne (DBCO) functional group or an azide functional group. Lane 1 shows the ssDNA before labeling; lane 2 shows the 5'-abasic ssDNA created by enzyme excision; and lanes 3 and 4 show the ssDNA samples labeled with a DBCO or an azide, respectively.

The results of 5'-end labeling of ssDNA with an azide or a DBCO were shown in FIG. 7, where lane 1 shows the ssDNA substrate before the modification, lane 2 shows the 5'-abasic ssDNA created by enzyme excision, and lanes 3 and 4 show the ssDNA samples modified with a DBCO and an azide, respectively.

Example 7. 5'-End Labeling of ssDNA with a Maleimide Group

The 5'-end labeling of a 45-mer single-stranded DNA (ssDNA; SEQ ID NO: 1) with a maleimide group was first carried out with 100 nM of ssDNA, 1 mM of uracil-DNA glycosylase, and 200 µM of aminooxy-PEG-azide in the reaction buffer containing 1 mM Tris-HCl (pH 8.0), 5 mM NaCl, 10 µM EDTA, and 0.02% PEG-4000. The DNA labeling reactions were performed at 37° C. for 60 min and then stopped by the addition of equal volume (10 mL) of 2× quench solution. The 5'-azide labeled ssDNA was purified using the QIAquick Nucleotide Removal Kit (Qiagen, Waltham, MA, U.S.A.). To label a maleimide group, the purified 5'-azide labeled ssDNA was further reacted with 200 µM of DBCO-PEG-maleimide. The reaction was performed at 37° C. for 60 min and then stopped by the addition of equal volume (10 mL) of 2× quench solution. The reaction products of 5'-labeled ssDNA were analyzed by 20% polyacrylamide gel electrophoresis (PAGE) containing 8 M urea. The gel was first stained with 1×SYBR Gold Nucleic Acid Gel Stain solution (ThermoFisher Scientific, Waltham, MA, U.S.A.) and visualized by scanning the gel at Amersham Typhoon Biomolecular Imagers (Marlborough, MA, U.S.A.).

Figure 8:
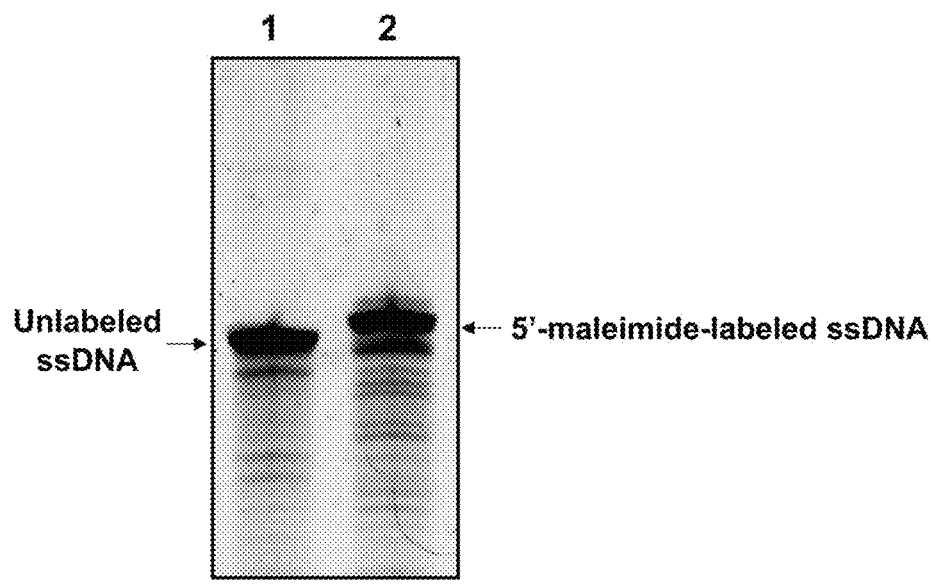
FIG. 8 shows the urea-PAGE result of 5'-end labeling on a single-stranded DNA (ssDNA) with a maleimide group. Lane 1 shows the ssDNA before labeling, and lane 2 shows the ssDNA labeled with a maleimide group.

The results of 5'-end labeling of ssDNA with a maleimide group was shown in FIG. 8, where lane 1 shows the ssDNA substrate before the modification, and lane 2 shows the ssDNA sample labeled with a maleimide group.

Example 8. Purification of 5'-End Labeled ssDNA by Ion-Pair Reversed-Phase High Performance Liquid Chromatography (IPRP-HPLC)

Figure 9:
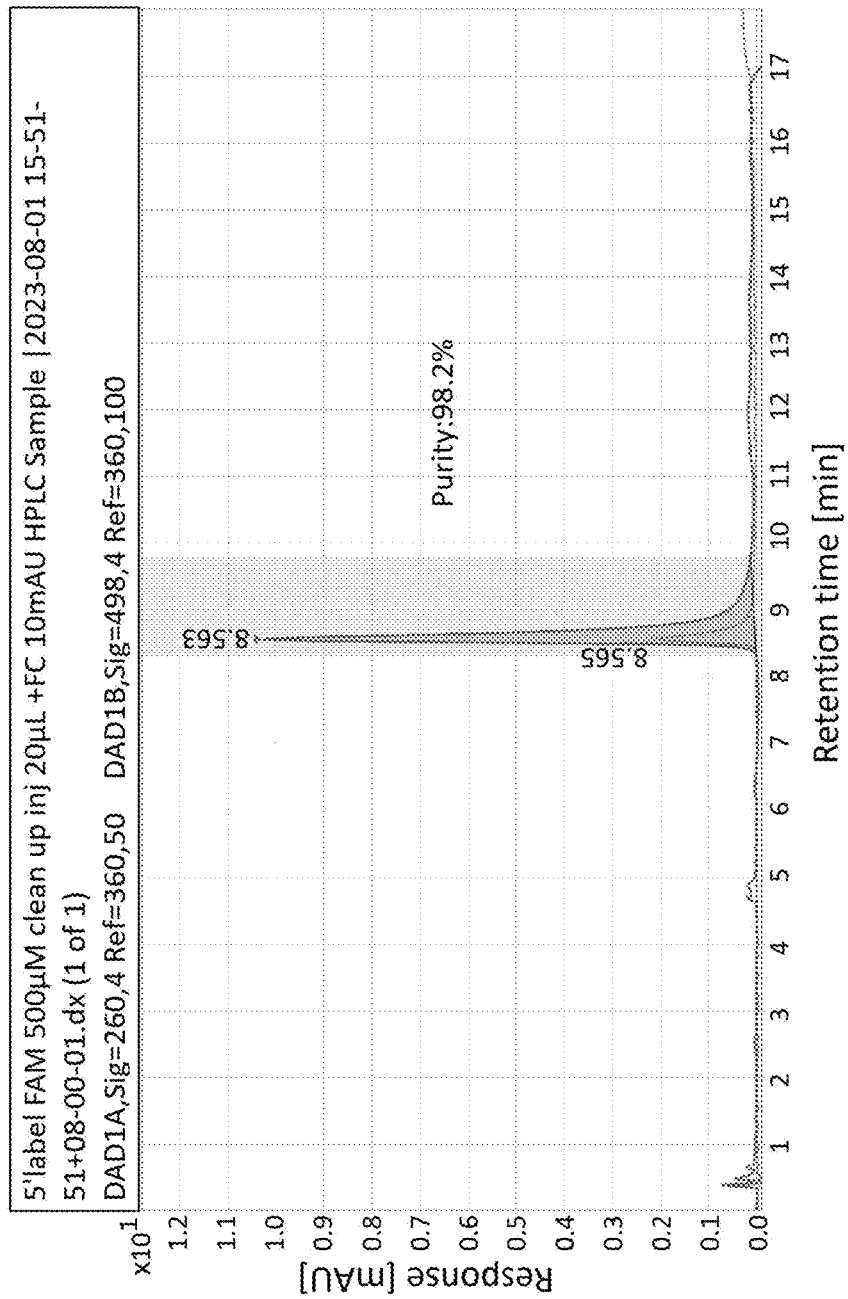
FIG. 9 shows the result of HPLC purification of 5'-labeled ssDNA with a 5(6)-FAM dye. The estimated purity of the labeled ssDNA as determined by the peak area at $\lambda=260$ nm is about 98.2%.
Figure 10:
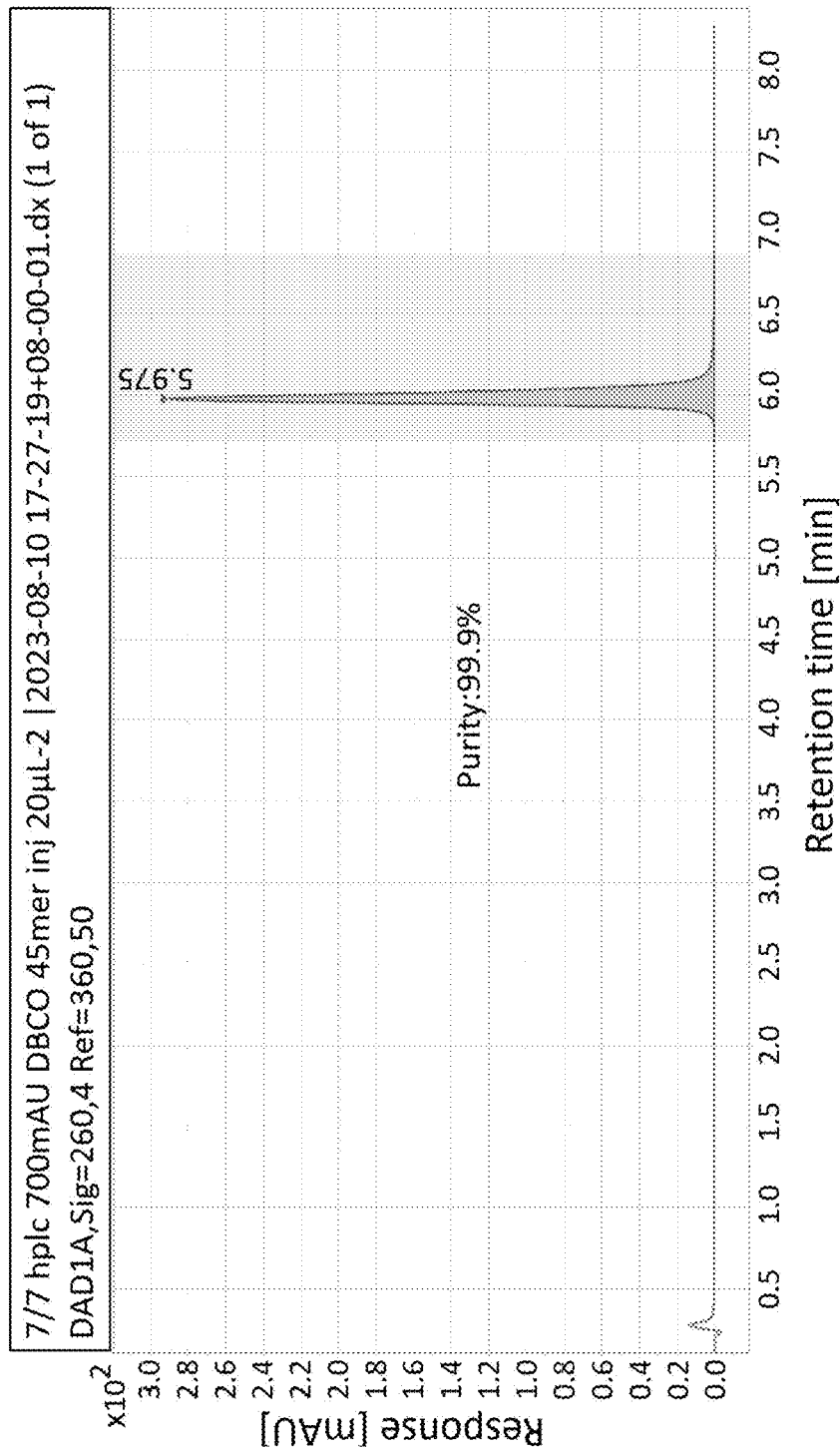
FIG. 10 shows the result of HPLC purification of 5'-labeled ssDNA with dibenzylcyclooctyne (DBCO). The estimated purity of labeled ssDNA as determined by the peak area at $\lambda=260$ nm is about 99.9%.
Figure 11:
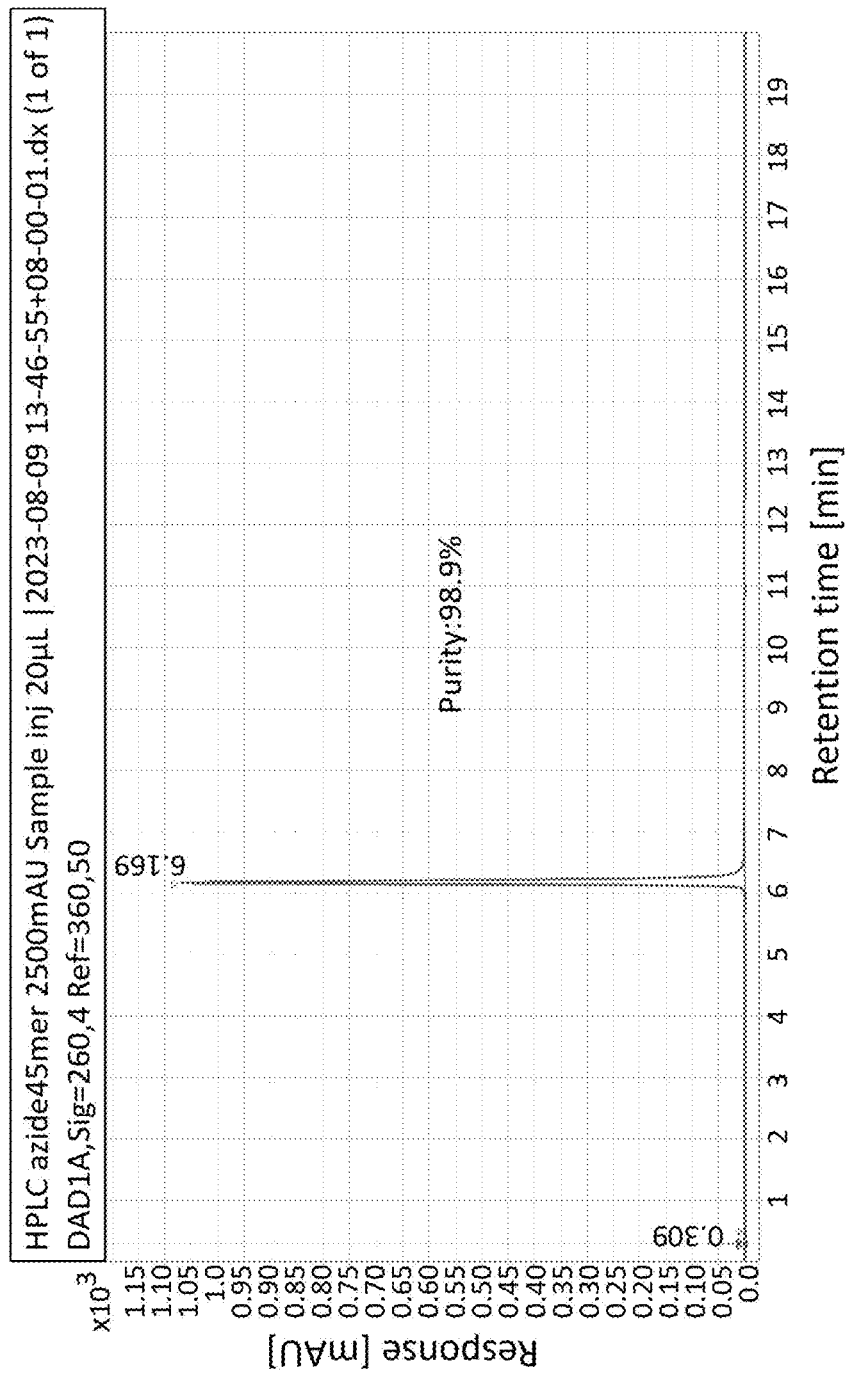
FIG. 11 shows the result of HPLC purification of 5'-labeled ssDNA with an azide group. The estimated purity of labeled ssDNA as determined by the peak area at □=260 nm is about 98.9%.

To confirm the purity of 5'-end labeling products, the 5'-end labeled ssDNA was further purified by high performance liquid chromatography (HPLC). Briefly, the 5'-labeled ssDNA was first cleaned up by QIAquick Nucleotide Removal Kit (Qiagen, Waltham, MA, U.S.A.). The cleanup sample was then purified via AdvanceBio Oligonucleotide (2.1×50 mm) column using Agilent 1260 Infinity II Bio-Inert LC System (Santa Clara, CA, U.S.A.). The desired 5'-labeled ssDNA was eluted from the column using different gradients of mobile phase, which was formed by mixing two separate components, solvent A (50 mM TEAA dissolved in deionized water) and solvent B (100 mM TEAA dissolved in acetonitrile). The mobile phase gradient was implemented according to the following program: from 0 to 9 minutes, increasing the solvent B concentration from 8% to 15%; from 9 to 15 minutes, increasing the solvent B concentration from 15% to 30%; and from 15 to 18 minutes, decreasing the solvent B concentration from 30% to 8%. The column flow rate was maintained at 0.6 mL/min, and the column temperature was kept at 65° C. The sample injection volume was in the range of from 10 µL to 20 µL. The sample fractions were monitored by the absorbance values at the wavelengths of both 260 nm and 498 nm, with a peak width>0.05 minutes (5 Hz). The column fractions containing 5'-labeled ssDNA were pooled together and further concentrated by a centrifugal vacuum concentrator. The results, as shown in FIGS. 9 to 11, indicate that the 5'-end labeling methods of the present disclosure deliver highly pure 5'-end labeled ssDNA products with FAM, DBCO, and azide, respectively.

Example 9. Analysis of 5'-Labeled ssDNA by MALDI-TOF Mass Spectrometry

Figure 12:
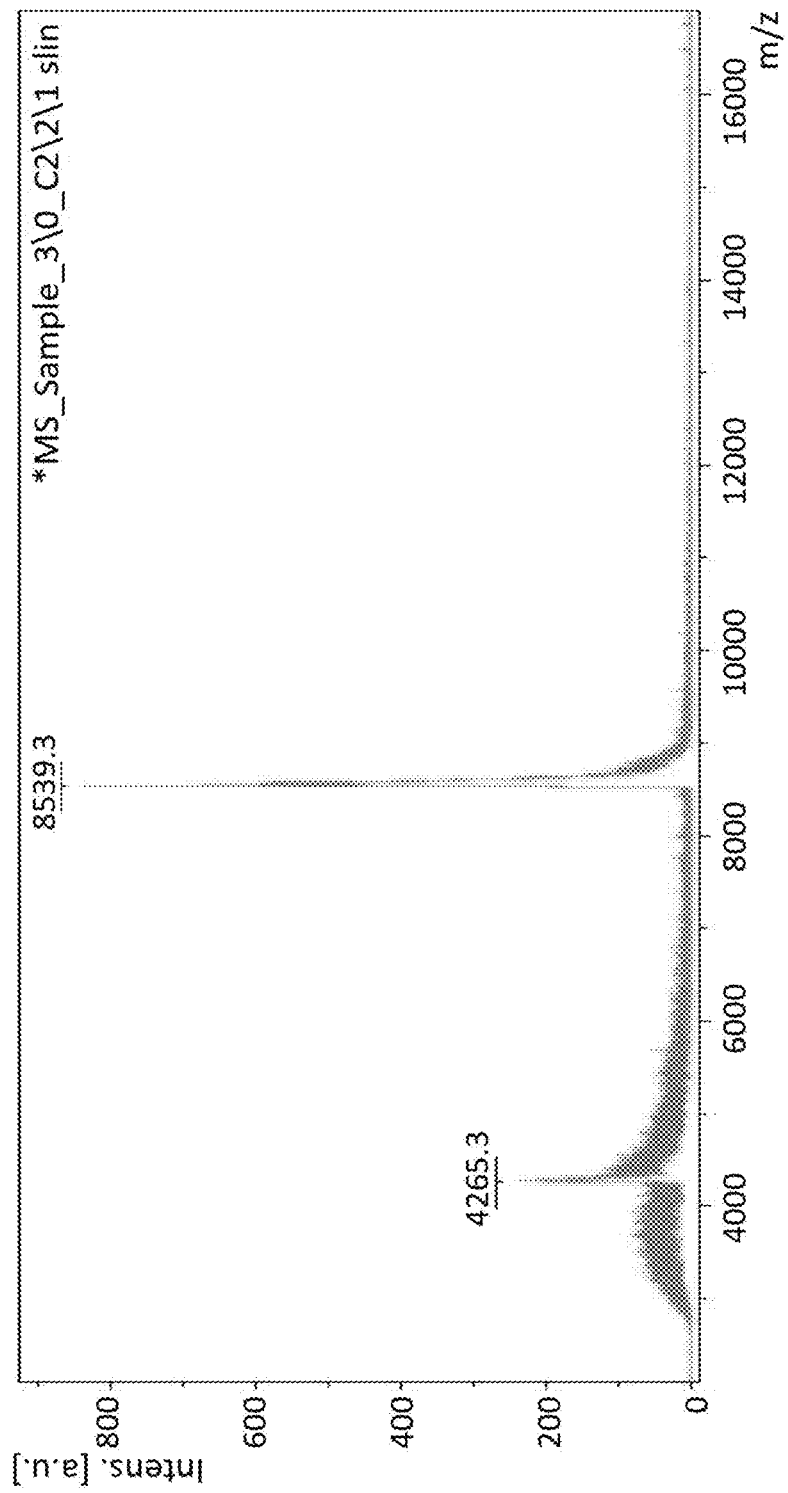
FIG. 12 shows the result of MALDI-TOF mass spectrum of HPLC-purified 5'-labeled ssDNA with a 5(6)-FAM dye. In the spectrum, both singly and doubly charged ions of the 5'-FAM-labeled oligonucleotides are identified at m/z 8539.3 and 4265.3, respectively.
Figure 13:
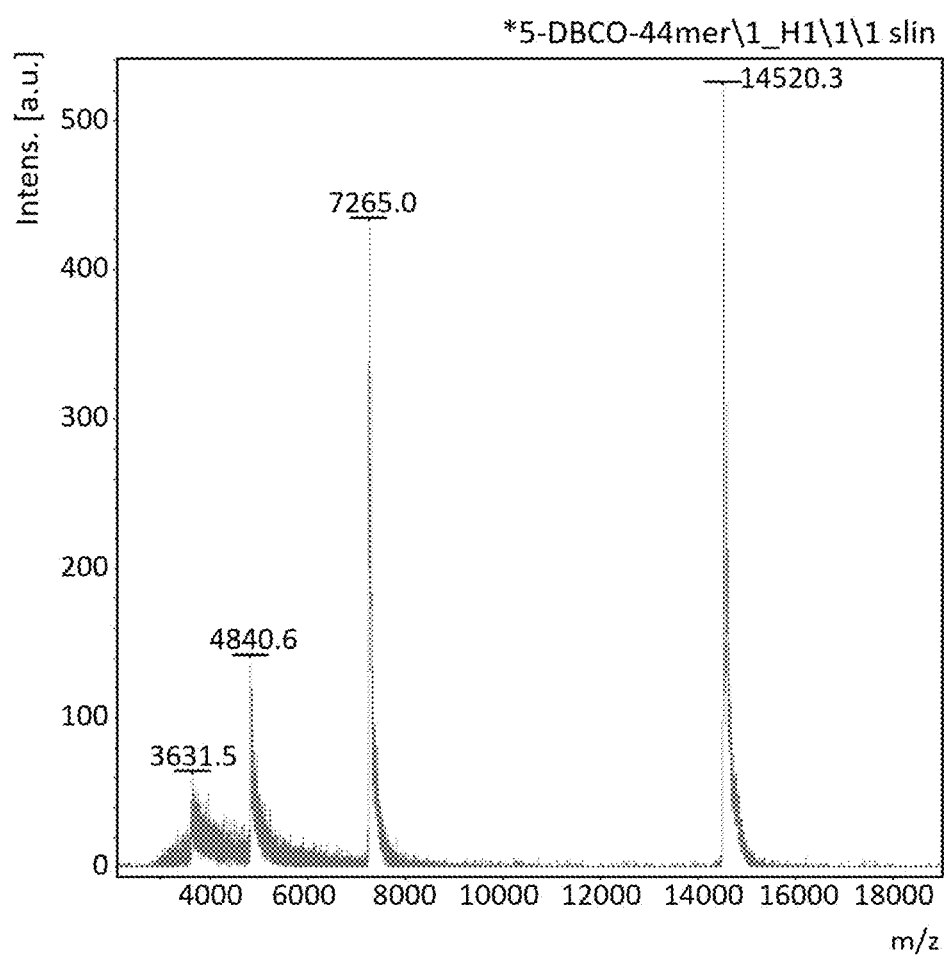
FIG. 13 shows the result of MALDI-TOF mass spectrum of HPLC-purified 5'-labeled ssDNA with dibenzylcyclooctyne (DBCO). In the spectrum, singly, doubly, triply, and quadruply charged ions of the 5'-DBCO-labeled oligonucleotides are identified at m/z 14520.3, 7265.0, 4840.6, and 3631.5, respectively.
Figure 14:
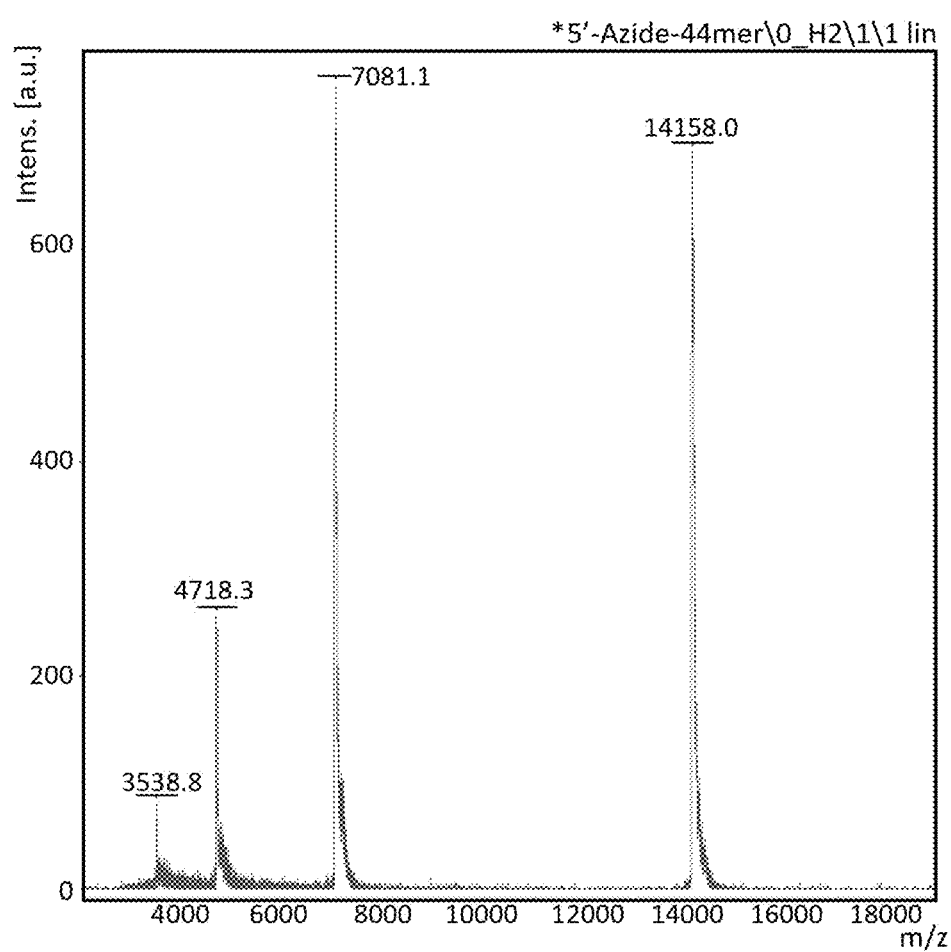
FIG. 14 shows the result of MALDI-TOF mass spectrum of HPLC-purified 5'-labeled ssDNA with an azide group. In the spectrum, singly, doubly, triply, and quadruply charged ions of the 5'-azide-labeled oligonucleotides are identified at m/z 14158.0, 7081.1, 4718.3, and 3538.8, respectively.

To further confirm the identity of 5'-end labeled products of the above reactions, the HPLC-purified 5'-end labeled ssDNA was further analyzed by MALDI-TOF (Matrix-Assisted Laser Desorption/Ionization Time-of-Flight) mass spectrometry. For sample preparation, the purified, dried 5'-labeled ssDNA was reconstituted in deionized water. After confirming that the instrument vacuum level reached a certain threshold and performing mass calibration, 1 µL of the matrix solution was dispensed onto an anchor chip plate (Bruker Daltonics, Billerica, MA, U.S.A.). The matrix solution was prepared by combining 200 µL of 50 mg/mL 3-hydroxypicolinic acid (3-HPA) solution with 10 µL of 100 mg/mL diammonium hydrogen citrate (DAC) solution and then diluted with 790 mL of deionized water to achieve a final concentration of 4 mg/mL 3-HPA and 0.2 mg/mL DAC. The plate was allowed to air dry at room temperature. Subsequently, 1 µL of the 5'-labeled ssDNA sample was applied to the matrix spot and allowed to air dry at room temperature. The mass spectra were acquired using a highly sensitive BRUKER microflex LRF20 MALDI-TOF mass spectrometer (Bruker Daltonics, Billerica, MA, U.S.A.). The instrument was configured to operate in positive ion linear mode, which allows for precise analysis of molecular ions. The selected mass range was set from 2,000 to 18,000, covering a broad spectrum of molecular masses. The results, as shown in FIGS. 12 to 14, indicate that the 5'-end labeling methods of the present disclosure deliver high purity and correct mass of 5'-end labeled ssDNA products with FAM, DBCO, and azide, respectively.

While some of the embodiments of the present disclosure have been described in detail in the above, it is, however, possible for those of ordinary skill in the art to make various modifications and changes to the embodiments shown without substantially departing from the teaching of the present disclosure. Such modifications and changes are encompassed in the scope of the present disclosure as set forth in the appended claims.

What is claimed is:

1. A kit for 5'-end labeling of a nucleic acid, comprising:
a 5'-end glycosylase, configured to create an intermediate nucleic acid having an abasic site at the 5'-end of the nucleic acid;
an aldehyde-reactive compound carrying a detectable label, configured to couple with the intermediate nucleic acid at the abasic site to form a labeled nucleic acid with the detectable label attached at the 5'-end; and
a 5' to 3' exonuclease, configured to remove an unlabeled nucleic acid and the intermediate nucleic acid.

2. The kit of claim 1, wherein the 5' to 3' exonuclease is selected from the group consisting of T5 exonuclease, T7 exonuclease, bacterial alkaline exonuclease, viral alkaline exonuclease, phage lambda exonuclease, exonuclease VIII, RecJ, RecJf, Tth RecJ, Mpn NrnA, human exonuclease 5, human exonuclease 1, SNM1, SNM1A, human SNM1B/Apollo, bovine SNM1B, SXT-Exo, phospholipase D3, phospholipase D4, Sso1391-Csa1, Sto0027-Csa1, Ttx1248-Csa1, Sso1451-Csa1, Sto2633-Csa1, Pfu1793-Cas4, Sto2501, Sso0001, Sto2331-Cas4, Ttx1245-Cas4, Sso1449-Cas4, Sto2635-Cas4, Sso1392-Cas4, SIRV2 gp19, bacterial AddB, and any combination thereof.

3. The kit of claim 1, wherein the 5' to 3' exonuclease comprises a 5'-exonuclease domain of DNA polymerase I.

4. The kit of claim 1, wherein the 5'-end glycosylase is selected from the group consisting of uracil-DNA glycosylase, alkyladenine DNA glycosylase, single-strand-selective monofunctional uracil-DNA glycosylase 1, methyl-binding domain glycosylase 4, thymine DNA glycosylase, MutY homolog DNA glycosylase, alkylpurine glycosylase C, alkylpurine glycosylase D, 8-oxo-guanine glycosylase 1 without an abasic site lyase activity, endonuclease III-like glycosylase 1 without the abasic site lyase activity, endonuclease VIII-like glycosylase 1 without the abasic site lyase activity, endonuclease VIII-like glycosylase 2 without the abasic site lyase activity, endonuclease VIII-like glycosylase 3 without the abasic site lyase activity, enzymatically active fragments thereof, and any combination thereof.

5. The kit of claim 4, wherein the uracil-DNA glycosylase is derived from a family of Micrococcaceae, Staphylococcaceae, or Caryophanaceae.

6. The kit of claim 1, wherein the detectable label is selected from the group consisting of an azide, an alkyne, a bicyclononyne, a dibenzocyclooctyne, a maleimide, a peptide, a protein, an antibody, a dendrimer, a biotin, a radioisotope, a photochromic dye, a fluorescent dye, a luminescent dye, and any combination thereof.

7. The kit of claim 1, wherein the aldehyde-reactive compound is a compound having at least one primary amine, a hydrazide, an acylhydrazide, a compound having an aminooxy group, a compound having a naphthalene-containing aminooxy group, or a compound having a guanidine-containing aminooxy group.

8. The kit of claim 1, wherein the aldehyde-reactive compound is a hydroxylamine biotin, an aminooxy-poly(ethylene glycol)-azide, an propargyl, an aminooxy-poly(ethylene glycol)-dibenzocyclooctyne, an aminooxy-poly(ethylene glycol)-bicyclononyne, a fluorescent dye-hydroxylamine, an aldehyde-reactive probe, an aminooxy-fluorescent dye, an aminooxy-biotin, a naphthalene-containing aminooxy-fluorescent dye, a guanidine-containing aminooxy-fluorescent dye, a fluorescent dye hydrazide, or a maleimide.

9. A method for 5'-end labeling of a nucleic acid, comprising:
providing a target nucleic acid to be labeled;
providing a 5'-end glycosylase to react with the target nucleic acid to create an intermediate nucleic acid having an abasic site at a 5'-end of the target nucleic acid;
providing an aldehyde-reactive compound carrying a detectable label for coupling with the intermediate nucleic acid at the abasic site to form a labeled nucleic acid with the detectable label attached at the 5'-end; and
providing a 5' to 3' exonuclease to remove an unlabeled target nucleic acid and the intermediate nucleic acid.

10. The method of claim 9, wherein the 5'-end glycosylase is selected from the group consisting of uracil-DNA glycosylase, alkyladenine DNA glycosylase, single-strand-selective monofunctional uracil-DNA glycosylase 1, methyl-binding domain glycosylase 4, thymine DNA glycosylase, MutY homolog DNA glycosylase, alkylpurine glycosylase C, alkylpurine glycosylase D, 8-oxo-guanine glycosylase 1 without an abasic site lyase activity, endonuclease III-like glycosylase 1 without the abasic site lyase activity, endonuclease VIII-like glycosylase 1 without the abasic site lyase activity, endonuclease VIII-like glycosylase 2 without the abasic site lyase activity, endonuclease VIII-like glycosylase 3 without the abasic site lyase activity, enzymatically active fragments thereof and any combination thereof.

11. The method of claim 9, wherein the aldehyde-reactive compound is a hydroxylamine biotin, an aminooxy-poly(ethylene glycol)-azide, an propargyl, an aminooxy-poly(ethylene glycol)-dibenzocyclooctyne, an aminooxy-poly(ethylene glycol)-bicyclononyne, a fluorescent dye-hydroxylamine, an aldehyde-reactive probe, an aminooxy-fluorescent dye, an aminooxy-biotin, a naphthalene-containing aminooxy-fluorescent dye, a guanidine-containing aminooxy-fluorescent dye, or a fluorescent dye hydrazide.

12. The method of claim 9, wherein the 5' to 3' exonuclease is selected from the group consisting of T5 exonuclease, T7 exonuclease, bacterial alkaline exonuclease, viral alkaline exonuclease, phage lambda exonuclease, 5'-exonuclease of DNA polymerase I, exonuclease VIII, RecJ, RecJf, Tth RecJ, Mpn NrnA, human exonuclease 5, human exonuclease 1, SNM1, SNM1A, human SNM1B/Apollo, bovine SNM1B, SXT-Exo, phospholipase D3, phospholipase D4, Sso1391-Csa1, Sto0027-Csa1, Ttx1248-Csa1, Sso1451-Csa1, Sto2633-Csa1, Pfu1793-Cas4, Sto2501, Sso0001, Sto2331-Cas4, Ttx1245-Cas4, Sso1449-Cas4, Sto2635-Cas4, Sso1392-Cas4, SIRV2 gp19, bacterial AddB, and any combination thereof.

13. The method of claim 9, wherein the target nucleic acid is single-stranded or comprises at least a duplex region formed by two complementary strands of nucleic acid.

14. The method of claim 9, wherein the target nucleic acid is a DNA or an RNA.

15. The method of claim 9, wherein the target nucleic acid is synthesized de novo or derived from a biological organism.

16. The method of claim 9, wherein the target nucleic acid comprises a uracil residue at the 5'-end.

17. A system for 5'-end labeling of nucleic acids, comprising a reaction reservoir, a liquid handling device, a temperature control unit, and a time control unit, wherein the liquid handling device is configured to:
  transfer a 5'-end glycosylase and an aldehyde-reactive compound to react with the nucleic acids in the reaction reservoir for a period of time at a defined temperature controlled by the temperature control unit, wherein the 5'-end glycosylase is configured to create an intermediate nucleic acid having an abasic site at the 5'-end of the nucleic acid, and the aldehyde-reactive compound is configured to couple with the intermediate nucleic acid at the abasic site to form a labeled nucleic acid with the detectable label attached at the 5'-end;
  transfer a 5' to 3' exonuclease to the reaction reservoir to remove an unlabeled nucleic acid and the intermediate nucleic acid.

* * * * *